United States Patent
Varghese et al.

(10) Patent No.: US 11,129,675 B2
(45) Date of Patent: Sep. 28, 2021

(54) NON-INVASIVE DEVICE FOR TREATMENT OF THE SKIN USING LASER LIGHT

(71) Applicant: KONINKLIJKE PHILIPS N.V., Eindhoven (NL)

(72) Inventors: Babu Varghese, Eindhoven (NL); Rieko Verhagen, Eindhoven (NL); Jonathan Alambra Palero, Eindhoven (NL); Martin Jurna, Eindhoven (NL); Margaret Ruth Horton, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 684 days.

(21) Appl. No.: 14/786,208

(22) PCT Filed: Apr. 24, 2014

(86) PCT No.: PCT/EP2014/058335
§ 371 (c)(1),
(2) Date: Oct. 22, 2015

(87) PCT Pub. No.: WO2014/174010
PCT Pub. Date: Oct. 30, 2014

(65) Prior Publication Data
US 2016/0074116 A1    Mar. 17, 2016

(30) Foreign Application Priority Data
Apr. 25, 2013 (EP) .................... 13165305

(51) Int. Cl.
*A61B 18/20* (2006.01)
*A61B 18/00* (2006.01)
*A61B 17/00* (2006.01)

(52) U.S. Cl.
CPC .. *A61B 18/203* (2013.01); *A61B 2017/00176* (2013.01); *A61B 2018/0047* (2013.01);
(Continued)

(58) Field of Classification Search
CPC ........... A61B 2017/00022; A61B 2017/00057; A61B 2017/00176; A61B 2017/00747;
(Continued)

(56) References Cited

U.S. PATENT DOCUMENTS 5,829,448 A * 11/1998 Fisher ................ A61K 41/0057
604/20
6,008,897 A * 12/1999 Sabsabi ................ G01N 21/718
356/318

(Continued)

FOREIGN PATENT DOCUMENTS

EP    0933096 A2    8/1999
EP    1693016 A1    8/2006

(Continued)

OTHER PUBLICATIONS

Kormashko et al, "Simulation of material removal efficiency with ultrashort laser pulses", Appl Phys A, 69 [Suppl], 1999 pp. 595-598.*

(Continued)

*Primary Examiner* — Scott Luan

(57) ABSTRACT

The invention provides a non-invasive device (100) for treatment of skin tissue using laser light, and it provides a method and a computer program product. The non-invasive device comprises a light emission system (110) for generating a first laser pulse (130) and a subsequent second laser pulse (150) at a predefined time delay ($\Delta T$) after the first laser pulse. The non-invasive device further comprises an optical system (160) for focusing, in use, the first laser pulse and the second laser pulse at a treatment location (210)

(Continued)

inside the skin tissue (200). The first laser pulse comprises a first power density, a first pulse duration and a first pulse energy for initiating a plasma (205) at the treatment location. The subsequent second laser pulse comprises a second power density being lower than the first power density and a second pulse duration being at least 10 times longer than the first pulse duration, and a second pulse energy higher than the first pulse energy for sustaining or intensifying the plasma initiated by the first laser pulse, whereby in use the first laser pulse and the second laser pulse together induce Laser Induced Optical Breakdown at the treatment location.

8 Claims, 4 Drawing Sheets

(52) U.S. Cl.
CPC ............. *A61B 2018/0088* (2013.01); *A61B 2018/00458* (2013.01); *A61B 2018/00642* (2013.01); *A61B 2018/00702* (2013.01); *A61B 2018/00761* (2013.01)

(58) Field of Classification Search
CPC .......... A61B 2017/00761; A61B 18/20; A61B 18/203; A61B 2018/00452; A61B 2018/00458; A61B 2018/00047; A61B 2018/00571; A61B 2018/00577; A61B 2018/00625; A61B 2018/00642; A61B 2018/00648; A61B 2018/00702; A61B 2018/00761; A61B 2018/00779; A61B 2018/0088
USPC .................................................. 606/3, 9–13
See application file for complete search history.

(56) References Cited

U.S. PATENT DOCUMENTS

| | | | |
|---|---|---|---|
| 6,159,204 A | 12/2000 | Hibst | |
| 6,193,711 B1 | 2/2001 | Connors | |
| 6,394,788 B1 | 5/2002 | Early | |
| 6,661,511 B2 | 12/2003 | Detalle | |
| 8,523,926 B2 * | 9/2013 | Neev | A61B 18/203 606/9 |
| 8,821,482 B2 * | 9/2014 | Verhagen | A61B 5/1077 606/11 |
| 2010/0063490 A1 * | 3/2010 | Verhagen | A61B 5/1077 606/9 |
| 2015/0080863 A1 * | 3/2015 | Welches | A61B 18/20 606/3 |

FOREIGN PATENT DOCUMENTS

| | | |
|---|---|---|
| JP | S6266846 | 3/1987 |
| JP | H09238918 | 9/1997 |
| WO | 0043755 A1 | 7/2000 |
| WO | 2007126999 A2 | 11/2007 |
| WO | 2008001284 A2 | 1/2008 |
| WO | 2010065645 A2 | 6/2010 |
| WO | 2010150175 A1 | 12/2010 |
| WO | 2012107830 A1 | 8/2012 |

OTHER PUBLICATIONS

Yang, et al: "Absorption of Laser Light in Overdense Plasmas" by Sheath Inverse Bremsstrahlung, Nov. 1994.
Schlessinger, et al: "Inverse Bremsstrahlung Absorption Rate in an Intense Laser Field", Nov. 1978.
Weng, et al: "Inverse bremsstrahlung absorption with full electron-electron collisions operator", Journal of Physics: Conference Series 112 (2008).
Berthe, et al: "Experimental study of the transmission of breakdown plasma generated during laser shock processing", Eur. Phys. J. AP 3, 215-218 (1998).
Hernandez-Rueda, et al: "Ultrafast time-resolved spectroscopy of a fs-laser-induced plasma inside glass using a super-continuum probe beam", Applied Physics A (2019) 125:591.

* cited by examiner ns and a second pulse
NON-INVASIVE DEVICE FOR TREATMENT OF THE SKIN USING LASER LIGHT This application is the U.S. National Phase application under 35 U.S.C. § 371 of International Application No. PCT/EP2014/058335, filed on Apr. 24, 2014, which claims the benefit of European Application No. 13165305.7 filed on Apr. 25, 2013. These applications are hereby incorporated by reference herein.

FIELD OF THE INVENTION

This invention relates to a non-invasive device for treatment of skin tissue using laser light.

This invention further relates to a method for skin treatment.

BACKGROUND OF THE INVENTION

Such non-invasive skin treatment device is, e.g., known from the published international patent application WO 2008/001284 A2. Said application discloses a skin treatment device with a laser source and focusing optics. The device creates a focal spot in a dermis layer of the skin to be treated. The power of the laser is selected such that laser-induced optical breakdown (LIOB) affects the skin in order to stimulate re-growth of skin tissue and reduce wrinkles.

The device is able to provide a laser-induced optical breakdown (LIOB) phenomenon in the skin by providing sufficiently intense laser pulses. This LIOB is based on strong non-linear absorption of the laser light by the skin tissue, which occurs above a certain threshold value for the power density of the laser light. This strong absorption causes a very localized plasma that is able to damage or even remove tissue at the location of said plasma. The effect is local, because below the threshold there is zero or very little linear and non-linear absorption, while above the threshold a plasma is generated.

LIOB occurs inside the skin tissue when the light intensity is sufficiently high to produce a critical free-electron density, which is about $10^{21}$ cm$^{-3}$. To generate such high intensity locally inside the skin, the requirements on the light source to create LIOB are relatively high.

OBJECT OF THE INVENTION

It is an object of the invention to provide a device for light-based skin treatment in which the requirements on the light source are reduced.

SUMMARY OF THE INVENTION

A first aspect of the invention provides a non-invasive device for treatment of skin using laser light. A second aspect of the invention provides a skin treatment method.

The non-invasive device for treatment of skin according to the first aspect of the invention comprises a light emission system for generating a first laser pulse and a subsequent second laser pulse at a predefined time delay after the first laser pulse. The non-invasive device further comprises an optical system for focusing, in use, the first laser pulse and the second laser pulse into a focal spot at a treatment location inside the skin tissue. The first laser pulse has a first power density (W/cm$^2$) in the focal spot, a first pulse duration and a first pulse energy (mJ) for initiating a plasma at the treatment location in the skin tissue at the treatment location. The subsequent second laser pulse has a second power density in the focal spot being lower than the first power density, a second pulse duration being at least 10 times longer than the first pulse duration, and a second pulse energy higher than the first pulse energy for sustaining or intensifying, by generating the second laser pulse at said predefined time delay after the first laser pulse, the plasma initiated by the first laser pulse by absorption of at least part of the energy of the second laser pulse by the plasma initiated by the first laser pulse to generate breakdown of the skin tissue in the treatment location. It is in this manner that, in use, the first laser pulse and the second laser pulse together generate Laser-Induced Optical Breakdown at the treatment location.

The use of two laser pulses to generate Laser-Induced Optical Breakdown (further also indicated as LIOB) relaxes the boundary conditions of the light emission system significantly. The first laser pulse creates a plasma at the treatment location inside the skin tissue, and the second laser pulse sustains or even enhances (or feeds) this plasma created by the first laser pulse. This combination of the first laser pulse and the second laser pulse creates a sufficiently high electron density at the treatment location to generate LIOB. In the known non-invasive LIOB system, LIOB is usually produced using a single laser pulse. A laser source capable to produce this single laser pulse in the known LIOB system must be able to produce a relatively short laser pulse (pulse duration less than 1,000 picoseconds) having a relatively high energy (up to 10 mJ). This combination of requirements to generate the single laser pulse in the known non-invasive LIOB system causes the known laser source to be relatively bulky, such as an industrially used Nd:YAG laser source. Using such a laser source in the known non-invasive LIOB systems makes the known LIOB systems relatively expensive and causes the operation of such LIOB system to require specialists that know how to operate such a high-power laser source. The inventors have found that by splitting up the LIOB generation between the first laser pulse and the second laser pulse, the boundary conditions of each of the first laser pulse and the second laser pulse may be relaxed significantly such that also the requirements on the light emission system may be relaxed significantly, thereby reducing the overall cost of the non-invasive skin treatment device significantly. For example, the light emission system may comprise two different laser sources which produce, respectively, the first laser pulse and the subsequent second laser pulse. The first pulse duration (or first pulse width) of the first laser pulse may, for example, be 10 times shorter than the second pulse duration (or second pulse width), or even up to 500 to 1,000 times shorter than the second pulse duration (or second pulse width) of the second laser pulse. The first power density of the first pulse is higher than the second power density of the second pulse, while the overall energy of the second laser pulse is approximately 10 to 100 times higher than the energy of the first laser pulse. Because the requirements for the first laser pulse and the second laser pulse are so different, the two different laser sources may be specifically tuned to produce these first laser pulses and second laser pulses, which results in a more cost-effective solution. But, in addition to a reduction in costs, the non-invasive device may also become less bulky, which may also be an important aspect for the consumer market. Furthermore, the device may be able to be operated by non-specialists, because the individual laser power to produce the first laser pulse and the second laser pulse is significantly less than the laser power required for the single laser pulse LIOB generation, which is approximately a factor of 20 higher than the highest power of the first laser pulse or the second laser pulse.

This reduction in individual laser power to produce the first laser pulse and the second laser pulse in the non-invasive device according to the invention has the further benefit that it reduces any possible damage to the skin tissue, which would be due to the treatment of the skin using such high power laser light, and that it reduces any possible damage of optical elements guiding the first laser pulse and the second laser pulse to the skin tissue.

In the non-invasive device according to the invention, the second laser pulse is emitted at the predefined time delay after the first laser pulse. A benefit of delaying the second laser pulse after the first laser pulse is that the absorption efficiency of the second laser pulse by the plasma generated by the first laser pulse is improved. Because some time is required for the first laser pulse to generate the plasma at the treatment location, the delay of the second laser pulse will ensure that the second laser pulse arrives at the treatment location when the plasma is 'ready' to absorb the radiation of the second laser pulse. The exact time delay required to achieve the highest efficiency may be experimentally determined and may differ depending on the depth inside the skin where the treatment location is located.

In an embodiment of the non-invasive device according to the invention, the first pulse duration (or first pulse width) is in a range between 1 and 1,000 picoseconds, and the second pulse duration (or second pulse width) is in a range between 1 and 1,000 nanoseconds. The first pulse duration or first pulse width and the second pulse duration or second pulse width are typically measured at the Full Width Half Maximum (further also indicted as FWHM) of the first laser pulse and second laser pulse, respectively. In a further embodiment of the non-invasive device according to the invention, the first pulse energy is in a range between 0.1 and 2 mJ, and the second pulse energy is in a range between 1 and 200 mJ.

In an embodiment of the non-invasive device according to the invention, the time delay between the first laser pulse and the second laser pulse is in a range between 1 nanosecond and 10 microseconds. The time delay is typically measured from a maximum intensity of the first laser pulse to a maximum intensity of the second laser pulse. Therefore, the first laser pulse and the second laser pulse may partially overlap. As indicated before, the effect of the time delay is that the efficiency of the absorption of the light of the second light pulse by the plasma is enhanced due to the fact that some time is required for the first light pulse to generate the plasma inside the skin tissue. Again, the exact value of the time delay required to achieve the highest efficiency may be experimentally determined and may differ depending on the depth inside the skin where the treatment location is located.

In an embodiment of the non-invasive device according to the invention, a wavelength of the second laser pulse is selected to generate off-resonance absorption of the energy of the second laser pulse by the plasma at the treatment location to sustain or intensify the plasma initiated by the first laser pulse. Or, put differently, the non-invasive device according to the invention is configured for emitting a wavelength of the second laser pulse which is selected to be included in an absorption peak of Inverse Bremsstrahlung of the plasma created by the first laser pulse. The second laser pulse may even enhance (or feed) the plasma created by the first laser pulse—as already mentioned before. Such off-resonance absorption is different from the on-resonance absorption where the wavelength of the plasma feeding light is tuned to the peak resonance absorption of the excited target atoms used, for example, for ablation. On-resonance absorption requires critical pulse parameters matching the energy levels of the target atoms or molecules. The energy is transferred to the targeted atoms, not to the plasma itself. In the current embodiment, off-resonance absorption is used for which substantially the only restriction to the wavelength of the second laser pulse is that the laser pulse efficiently reaches the plasma inside the skin tissue, initiated by the first laser pulse.

In an embodiment of the non-invasive device, the first laser pulse comprises polarized light. To be able to efficiently initiate a plasma at the treatment location inside the skin tissue, polarized laser light may be used. By choosing the first laser pulse to be a polarized first laser pulse, the efficiency of the initiation of the plasma at the treatment location inside the skin tissue may be further improved—allowing the peak intensity or peak power density of the first laser pulse to be further reduced. The subsequent, second laser pulse is used for sustaining or feeding the initiated plasma and there is no real benefit when this second laser pulse is polarized. In an embodiment of the non-invasive device, the wavelength of the first laser pulse is approximately 1064 nanometers. The wavelength of the second laser pulse may be any wavelength that reaches the plasma inside the skin.

In an embodiment of the non-invasive device, the light emission system comprises a first laser for emitting the first laser pulse and comprises a second laser for emitting the second laser pulse, the second laser being different from the first laser. As indicated before, the first laser pulse is different from the second laser pulse. Due to the use of the first laser pulse and the subsequent, second laser pulse, the individual requirements on each of the first laser pulse and the second laser pulse have already been reduced. As a result, the light emission system may already have relaxed boundary conditions in case the light is generated using a single laser. However, when using the first laser to generate the first laser pulse and the second laser to generate the second laser pulse, the first laser and the second laser may be specifically tuned to produce these first laser pulses and second laser pulses, respectively, which results in a more cost-effective solution.

In an embodiment of the non-invasive device, the treatment location is in a dermis layer of the skin, below the epidermis layer. Therefore, the wavelength used for the first laser pulse and the second laser pulse should reach this dermis layer inside the skin and should have sufficient intensity or power density at this dermis layer to ensure that the first laser pulse initiates the plasma and that the second laser pulse sustains or enhances (or feeds) the plasma sufficiently to generate enough critical free-electron density to achieve LIOB.

In an embodiment of the non-invasive device, the non-invasive device comprises a feedback system for determining a focusing depth of the first laser pulse and/or the second laser pulse at the treatment location. Such a feedback system may, for example, be configured for measuring a Second Harmonic Generated signal (further also indicated as SHG signal) reflected from the treatment location. This SHG signal may be a measure of the collagen content present at the treatment location and so the SHG signal measured may be used to see whether the optical system focuses inside the dermis layer. Collagen strains present in the dermis layer have birefringent characteristics, such that when hit by light, they reflect part of the light as a SHG signal. So, the measuring of the SHG signal may be used to determine whether the optical system focuses at the correct depth inside the skin. The SHG signal may be created using a further light source in the non-invasive device according to the invention. Alternatively, the SHG signal may be created using, for example, part of the impinging second laser pulse. According to an alternative method, the focusing depth is determined using polarization-sensitive birefringent detection for detecting the collagen strains in the dermis layer. Of course any other known feedback system for determining a focusing depth inside the skin may be used.

In an embodiment of the non-invasive device, the non-invasive device comprises a feedback system for detecting the plasma inside the skin tissue and/or for detecting an acoustic signal generated during the Laser-Induced Optical Breakdown at the treatment location. Detecting the plasma inside the skin tissue may, for example, be done by an optical detector, which detects light of a different wavelength than the wavelength of any of the first laser pulse and the second laser pulse, as the plasma will emit light in a very broad wavelength range. Detection of the presence of the plasma is an indicator of the efficiency of the LIOB. Alternatively, the feedback system may comprise an acoustic detector to detect the acoustic signal generated during LIOB. Due to the rapid initiation of the plasma and the creation of lesions, an acoustic wave will propagate through the skin tissue which may be detected using an acoustic detector and which may be used as a measure of the effectiveness of the LIOB process.

The method of skin treatment using laser light according to the second aspect of the invention comprises the steps of:
generating a first laser pulse,
generating a subsequent, second laser pulse different from the first laser pulse and at a predefined time delay after the first laser pulse, and
focusing the first laser pulse and the second laser pulse into a focal spot at a treatment location inside skin tissue.

The first laser pulse has a first power density (W/cm$^2$) in the focal spot, a first pulse duration, and a first pulse energy for initiating a plasma in the skin tissue at the treatment location. The subsequent, second laser pulse has a second power density in the focal spot being lower than the first power density, a second pulse duration being at least 10 times longer than the first pulse duration, and a second pulse energy higher than the first pulse energy for sustaining or intensifying, by generating the second laser pulse at said predefined time delay after the first laser pulse, the plasma initiated by the first laser pulse by absorption of at least part of the energy of the second laser pulse by the plasma initiated by the first laser pulse to generate breakdown of the skin tissue in the treatment location.

Thus, in use, the first laser pulse and the second laser pulse together generate Laser-Induced Optical Breakdown at the treatment location. As mentioned already hereinabove, the second laser pulse may also enhance or feed the plasma generated by the first laser pulse.

In an embodiment of the method, the first pulse duration (or first pulse width) is in a range between 1 and 1,000 picoseconds, and the second pulse duration (or second pulse width) is in a range between 1 and 1,000 nanoseconds. In a further embodiment of the method, the time delay is in a range between 1 nanosecond up to 10 microseconds. In another embodiment of the method, the first laser pulse is generated by a first laser and the second laser pulse is generated by a second laser different from the first laser.

These and other aspects of the invention are apparent from and will be elucidated with reference to the embodiments described hereinafter.

DETAILED DESCRIPTION OF THE INVENTION

Figure 1:
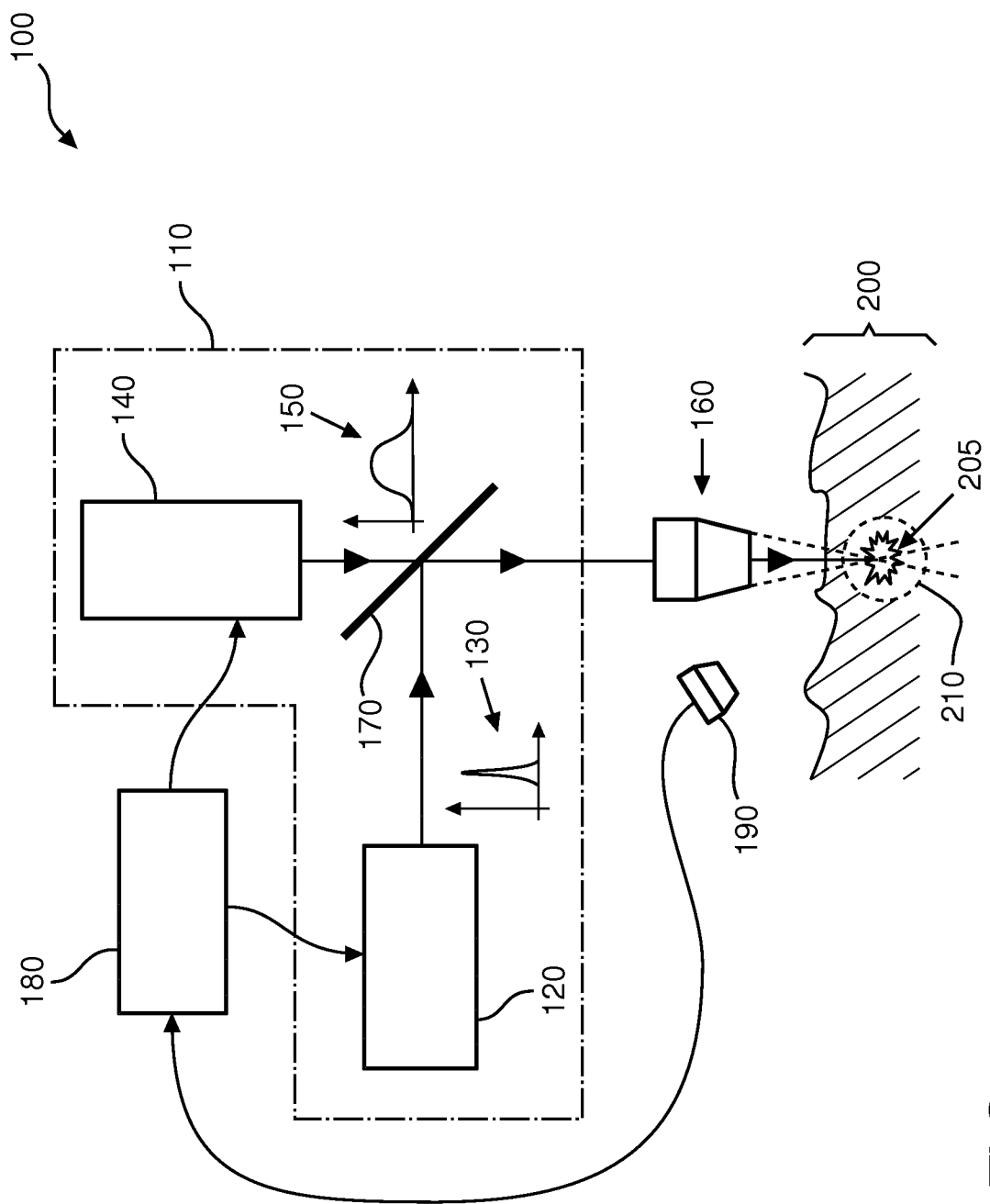
FIG. 1 schematically shows a non-invasive device according to the invention.

FIG. 1 schematically shows a non-invasive device 100 according to the invention. The non-invasive device 100 comprises a light emission system 110 for generating a first laser pulse 130 and a subsequent second laser pulse 150. The non-invasive device 100 further comprises an optical system 160, for example, a microscope objective 10 or any other lens element 160 for focusing the first laser pulse 130 and the second laser pulse 150 into a focal spot at a treatment location 210 inside the skin tissue 200. The first laser pulse 130 has a relatively high first power density (W/cm$^2$) in the focal spot, a relatively short first pulse duration (illustrated by means of the pulse shape indicated by reference number 130) and a first pulse energy. The first laser pulse 130 is configured such that a plasma is initiated in the skin tissue 200 in the focal spot at the treatment location 210. The second laser pulse 150 has a relatively low power density (W/cm$^2$) in the focal spot, a relatively long second pulse duration (illustrated by means of the pulse shape indicated by reference number 150), and a relatively high pulse energy. The second laser pulse 150 is configured for sustaining or feeding (or enhancing) the plasma initiated at the same treatment location by the first laser pulse 130 to create a sufficiently high free-electron density at the treatment location 210 to generate Laser-Induced Optical Breakdown (further also indicated as LIOB). For this purpose, the second laser pulse 150 is generated at a sufficiently short predefined time delay after the first laser pulse, such that after said time delay the plasma initiated by the first laser pulse 130 is still present and able to absorp the energy of the second laser pulse 150. The use of the first laser pulse 130 together with the subsequent second laser pulse 150 to generate LIOB relaxes the boundary conditions of the light emission system 110 significantly. In a known non-invasive LIOB system, LIOB is usually produced using a single laser pulse. This single laser pulse in the known LIOB system has a relatively short laser pulse duration (pulse duration less than 1,000 picoseconds) while having a relatively high energy (up to 10 milliJoules). This combination of requirements to generate the single laser pulse in the known non-invasive LIOB system causes the known laser source to be relatively bulky and expensive (applicable laser source may, for example, be an Nd:YAG laser source). Furthermore, such a high-power laser source in the known non-invasive LIOB system typically requires a specialist who knows how to operate such a laser source. The inventor has found that when the LIOB generation is split up between the first laser pulse 130 and the second laser pulse 150, the boundary conditions of each of the first laser pulse 130 and the second laser pulse 150 may be relaxed significantly such that also the requirements on the light emission system 110 may be relaxed significantly. This relaxation of the requirements on the light emission system 110 also reduces the cost of the non-invasive device 100 and may enable the non-invasive device 100 according to the invention to be operated by non-specialists. A specific range of requirements on the first laser pulse 130 and the second laser pulse 150 such that LIOB may be efficiently induced inside the Dermis layer 230 (see FIG. 2) may be found in Table 1 hereinbelow.

TABLE 1 overview of requirements on the single laser pulse LIOB and the LIOB solution using the first laser pulse 130 and the second laser pulse 150.

| | Single laser pulse LIOB Laser pulse | LIOB using the first laser pulse and the second laser pulse | |
|---|---|---|---|
| | | First laser pulse (Plasma ignition) | Second laser pulse (Plasma feeding) |
| Wavelength | 1064 nm | 1064 nm | Any wavelengths that could reach the plasma source generated inside the skin |
| Pulse duration | 1-200 ps | 1-1000 ps | 1-1000 ns |
| Pulse energy | 1-20 mJ | 0.1-2 mJ | 1-200 mJ |
| Mode profile | Single mode | Single mode/ Multi-mode | Single mode/ Multi mode |

In Table 1, the pulse duration range of the first laser pulse is relatively broad compared to the single laser pulse LIOB, while the overall pulse energy is relatively low compared to the single laser pulse LIOB. The correct combination of first laser pulse duration and overall pulse energy must be chosen to ensure that a plasma 205 will be initiated. For example, the inventors have found in experiments that the use of a first laser pulse having a pulse duration of, for example, 1,000 picoseconds with an overall pulse energy of 0.1 milliJoule will initiate a plasma 205, however this initiated plasma 205 may be a relatively low-density plasma without associated breakdown and lesion formation inside the skin tissue. The second laser pulse is required to enhance and feed the plasma 205 to ensure that LIOB occurs at the treatment location 210 inside the skin tissue 200.

Figure 3:
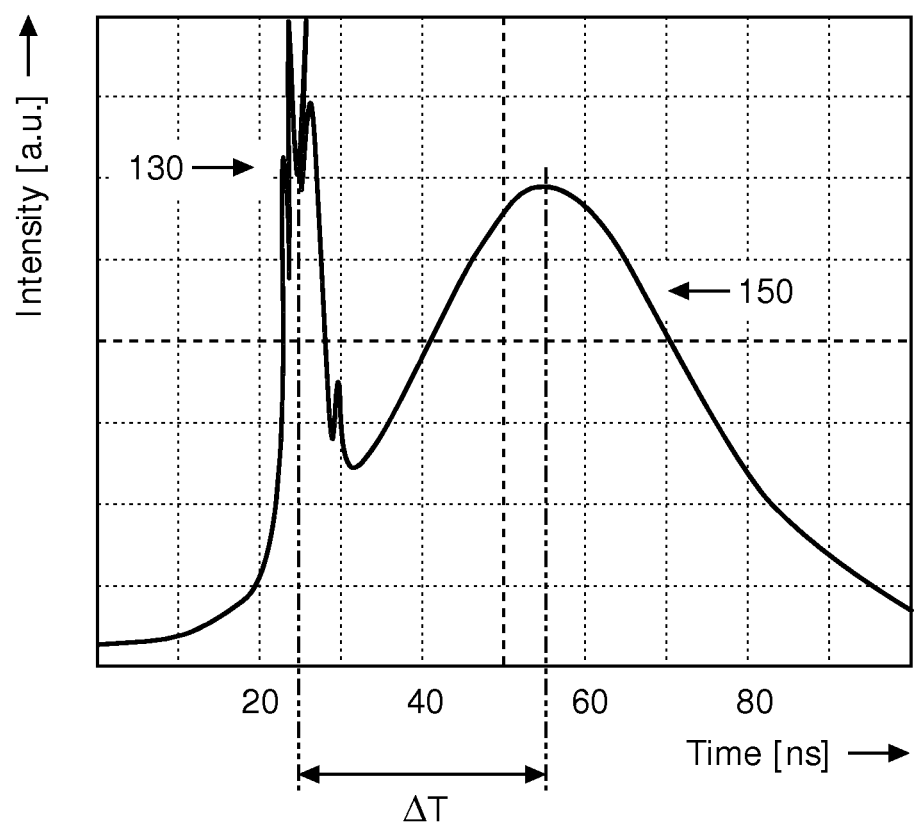
FIG. 3 shows the first laser pulse and the second laser pulse configured for jointly generating LIOB.

The light emission system 110 may, for example, comprise a first laser source 120 emitting the first laser pulse 130 and may, for example, comprise a second laser source 140 emitting the second laser pulse 150. The first pulse duration (or first pulse width) of the first laser pulse 130, for example, is 10 times shorter, or even much more shorter, such as 500 to 1,000 times shorter, compared to the second pulse duration (or second pulse width) of the second laser pulse 150, while the overall pulse energy of the second laser pulse 150 may be approximately 10 to 100 times higher than the overall pulse energy of the first laser pulse 130. An example of a possible first laser pulse 130 and a second laser pulse 150 is shown in FIG. 3 in which LIOB is demonstrated in water using two pulses. Because the requirements for the first laser pulse 130 and the second laser pulse 150 are so different, the first laser source 120 and the second laser source 140 may be specifically tuned to produce these first laser pulses 130 and second laser pulses 150, which results in a more cost-effective solution.

So, by using the light emission system 110 according to the invention, a reduction will be achieved of the maximum power and power density of the individual first laser pulse 130 and second laser pulse 150 necessary to generate the LIOB, compared to the laser pulse in the known non-invasive LIOB system. This reduction in individual laser power and power density also reduces any possible damage of the upper layers of the skin 200 (for example, the epidermis 220 layer—see FIG. 2) due to the treatment of the skin 200. Furthermore, the reduction of the maximum power and power density of the first laser pulse 130 and the second laser pulse 150 reduces any possible damage of optical elements 170, 160 guiding the first laser pulse 130 and the second laser pulse 150 to the skin 200.

The wavelength $\lambda f$ of the first laser pulse 130 may, for example, be 1064 nanometer, as light of this wavelength penetrates deeply into the skin 200. The wavelength $\lambda s$ of the second laser pulse 150 may comprise any wavelength that reaches the plasma 205 generated by the first laser pulse 130 and that sustains or feeds the plasma 205 to create the LIOB. This sustaining or feeding of the plasma 205 by the second laser pulse 150 may be done via off-resonance absorption or by tuning the second laser pulse 150 to emit light having a wavelength which is selected to be included in an absorption peak of Inverse Bremsstrahlung of the plasma 205 initiated by the first laser pulse 130.

In the non-invasive device 100 according to the invention, the second laser pulse 150 is emitted at the predefined time delay $\Delta T$ after the first laser pulse 130. Due to this time delay $\Delta T$, the efficiency of the absorption of the second laser pulse 150 by the plasma 205 initiated by the first laser pulse 130 is improved. When the first laser pulse 130 impinges on the treatment location 210, some time is required for the plasma 205 to be initiated at the treatment location 210. The time delay $\Delta T$ of the second laser pulse 150 relative to the first laser pulse 130 ensures that the second laser pulse 150 arrives at the treatment location 210 when the plasma 205 is 'ready' to absorb the radiation of the second laser pulse 150. The exact time delay $\Delta T$ required to achieve the highest efficiency may be experimentally established and may differ depending on skin type and depth inside the skin tissue where the treatment location 210 is located.

The non-invasive device 100 as shown in FIG. 1 also comprises optical elements 170, 160 to guide the first laser pulse 130 and the second laser pulse 150 to the treatment location 210. As indicated before, one of the optical elements 170, 160 may be an optical system 160 for focusing the first laser pulse 130 and the second laser pulse 150 into the skin tissue 200. Such optical system 160 may be, for example, a microscope objective 160. A further optical element may be, for example, a semi-transparent mirror element 170 to combine the first laser pulse 130 emitted by the first laser 120 with the second laser pulse 150 emitted by the second laser 140, such that they may use the same optical system 160. In addition to the two indicated optical elements 170, 160, the non-invasive device 100 may comprise other optical elements to shape and guide the first laser pulse 130 and the second laser pulse 150 to the treatment location 210 inside the skin tissue 200.

The non-invasive device 100 as shown in FIG. 1 further comprises a controller 180 for controlling the light emission system 110, for example, comprising the first laser 120 and the second laser 140, and it further comprises a feedback system 190 for providing some feedback signal to the controller 180 (indicated in FIG. 1 by means of the curved arrow going from the feedback system 190 to the controller 180). The controller 180 may, for example, determine the first pulse duration and the first power density of the first laser pulse 130 and the second pulse duration and the second power density of the second laser pulse 150, for example, to prevent damage to the upper layers of the skin tissue 200 during the non-invasive skin treatment. The controller 180 may also determine the time delay $\Delta T$ between the first laser pulse 130 and the second laser pulse 150 to further increase the efficiency of the generation of the LIOB by timing the time delay ΔT such that substantially all of the second laser pulse 150 is absorbed by the plasma 205. The controller 180 may also use the feedback signal of the feedback system 190 to determine, for example, the efficiency of the LIOB, initial damage to the upper layers of the skin tissue 200, and increased temperature of the upper layer of the skin tissue 200 or any other parameter useful to control the non-invasive device 100 according to the invention.

Figure 2:
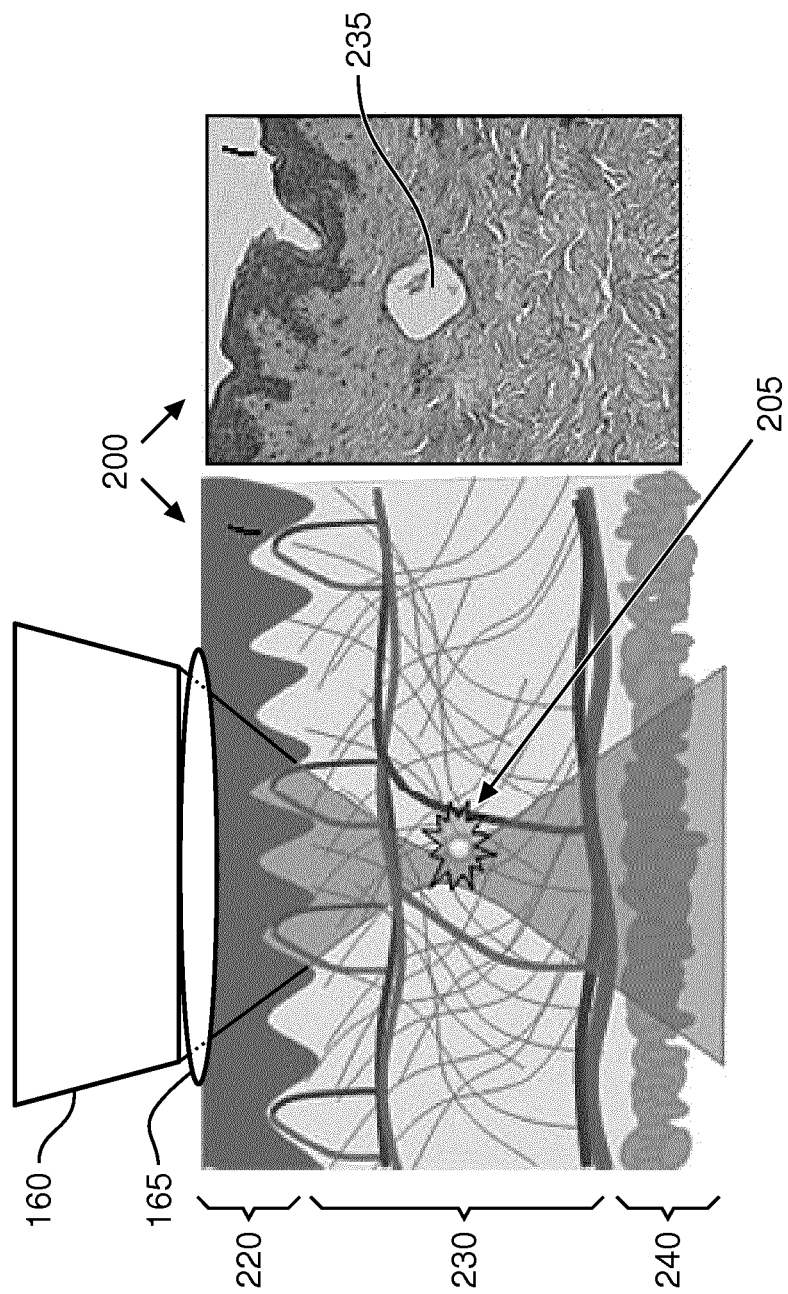
FIG. 2 shows some detail of the LIOB treatment in the Dermis layer.

FIG. 2 shows some detail of the LIOB treatment in the Dermis layer 230. LIOB treatment targets the Dermis layer 230 such that it affects the skin tissue 200 in order to stimulate re-growth of skin tissue and reduce wrinkles. The non-invasive device 100 is able to generate the LIOB phenomenon inside the skin 200 by providing a sequence of the first laser pulse 130 and the second laser pulse 150. In FIG. 2, part of the optical system 160 is shown from which the first laser pulse 130 and the second laser pulse 150 are focused inside the skin 200. Also indicated in FIG. 2 is an optical fluid 165 which typically is used to improve the optical coupling between the optical system 160 and the skin 200. Such optical fluid 165 typically has an index of refraction close to that of the skin 200 and a light exit window (not indicated) of the optical system 160 (see FIG. 1). It has a property whereby it overcomes the microscopic refractive index variations occurring at the skin surface due to vertically stacked corneocytes (not indicated). The refractive index of stratum corneum depends strongly on environmental conditions and recent history of the skin tissue 200 as well as on the age and skin care routine of an individual. A typical range of stratum corneum refractive index is from 1.47 to 1.5 under normal conditions, which is in the range of natural vegetable oils but slightly higher than that of mineral oils. So, the optical fluid 165 comprises oil 165, water 165 or any other fluid able to improve the optical coupling between the optical system 160 and the skin tissue 200. The first light pulse 130 and the subsequent second light pulse 150 are sequentially focused by the optical system 160 into the treatment location 210 in the Dermis layer 230. The first laser pulse 130 is configured for initiating a plasma 205 and the subsequent second laser pulse 150 is used to sustain or enhance the plasma 205 to generate LIOB at the treatment location 210. When the light is focused inside the Dermis layer 230, the surrounding tissue being the Epidermis layer 220 and the Sub-cutis layer 240 typically is not damaged, as the converging and diverging properties of the focused first light pulse 130 and second light pulse 150 typically have too low an intensity level.

The right-hand side image in FIG. 2 shows part of the skin tissue 200 in which a lesion 235 is shown created using the non-invasive device 100 according to the invention. Such a lesion 235 activates the skin 200 to stimulate re-growth of skin tissue, which will subsequently reduce wrinkles.

FIG. 3 shows the first laser pulse 130 and second laser pulse 150 configured for jointly generating LIOB. The example shown in FIG. 3 is an oscilloscope reading showing the parameters of the first laser pulse 130 and the second laser pulse 150 used to demonstrate the proof of the principle by creating optical breakdown in water. The wavelength $\lambda f$ of the light of the first laser pulse 130 and the wavelength $\lambda s$ of the second laser pulse 150 in this case are identical, being 1064 nanometers. The first pulse duration of the first laser pulse 130 is between 30 and 100 picoseconds at an overall pulse energy of 0.2 milliJoule for initiating the plasma inside water. The second pulse duration of the second laser pulse 150 is 10 to 20 nanoseconds at an overall pulse energy of 5 to 10 milliJoule for feeding the plasma 205 initiated by the first laser pulse 130. As can be seen from FIG. 3, the time delay ΔT between the peak intensity of the first laser pulse 130 and the peak intensity of the second laser pulse 150 is approximately 30 nanoseconds. As indicated before, the exact requirements (pulse duration, power density, overall pulse energy and time delay) to generate LIOB using the first laser pulse 130 and the second laser pulse 150 in skin tissue 200 may be different, depending on the depth inside the skin tissue 200 where the LIOB should occur. A table (not shown) indicating preferred settings in different situations or treatment depths may be generated, for example, experimentally. Such a table may, for example, be stored in the controller 180 (see FIG. 1) and used for selecting the preferred settings during operation.

Figure 4:
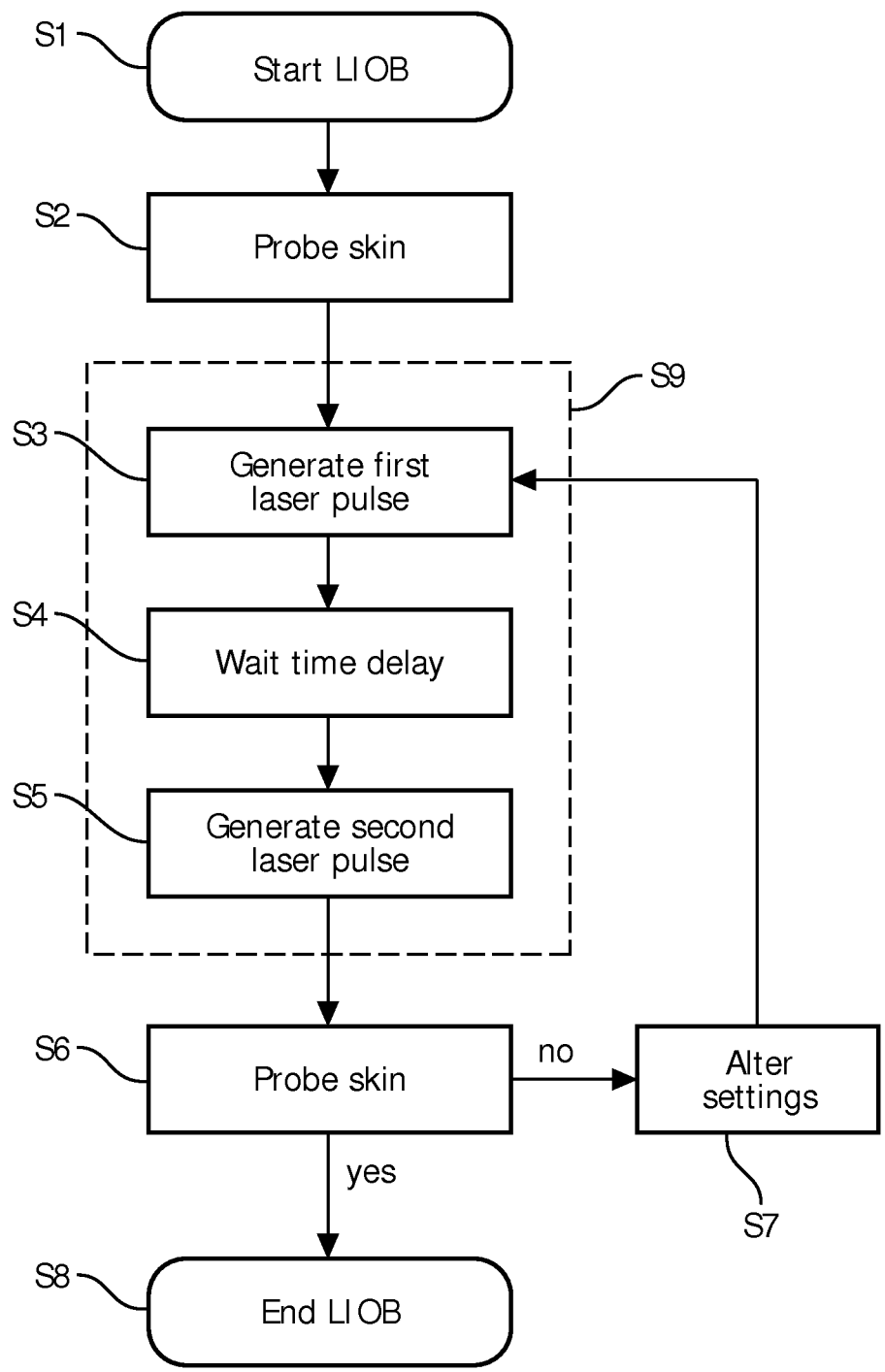
FIG. 4 shows a flow diagram indicating the method according to the invention and a computer program product configured to perform the method.

FIG. 4 shows a flow diagram indicating the method according to the invention and a computer program product configured to perform the method. At a first step S1, the LIOB process is started. Next, at step S2 the skin tissue 200 may be probed by a feedback system 190 (see FIG. 1). This probing step S2 may be a step during which the skin tissue 200 is analyzed before the skin treatment is started. During such probing step S2, the type of skin tissue 200 may be determined or the depth of wrinkles present in the skin tissue 200 may be determined before the Laser treatment is actually initiated. Although the probing step S2 is an optional step, it may enhance the overall quality of the skin treatment, as it enables the non-invasive device 100 to determine, for example, the characteristics of the first laser pulse 130 and the subsequent second laser pulse 150 to ensure that the LIOB treatment will be effective without, for example, damaging the upper dermis layer 220 (see FIG. 2). Next, in step S3, the first laser pulse 130 is generated after which the controller 180 waits for a predetermined time delay ΔT in step S4, after which, in step S5, the second laser pulse 150 is generated. This generation of the first laser pulse 130 may, for example, be done using the first laser 120 and the generation of the second laser pulse 150 may, for example, be done using the second laser 140. Together, steps S3, S4 and S5 cover LIOB step S9 covering the initiation of the plasma 205 (see FIG. 1), and the sustainment or enhancement of the plasma 205 to create the LIOB. Subsequently, in step S6 the skin tissue 200 may again be probed. Also, this probing of the skin tissue 200 may again be an optional step S6, for example, to determine an efficiency of the overall LIOB treatment and to determine whether or not to continue with the LIOB treatment. For example, when the LIOB treatment was not sufficient or when the LIOB treatment was not effective (indicated by the arrow comprising 'N'), the settings of the non-invasive device 100 may be altered in step S7 and the first laser pulse 130 may again be initiated in step S3 to redo the LIOB treatment at different settings. If the LIOB treatment was not sufficient, the LIOB treatment may be redone without changing the settings of the non-invasive device 100—so the sequence may be re-initiated in step S3 without different settings being applied in step S7. Alternatively, when the LIOB treatment was sufficient and effective (indicated by the arrow comprising 'Y'), the LIOB process may be ended at step S8.

It will be appreciated that the invention also extends to computer programs, particularly computer programs on or in a carrier, adapted for putting the invention into practice. The program may be in the form of source code, object code, a code intermediate source and object code such as a partially compiled form, or in any other form suitable for use in the implementation of the method according to the invention. It will also be appreciated that such a program may have many different architectural designs. For example, a program code implementing the functionality of the method or system according to the invention may be subdivided into one or more subroutines. Many different ways to distribute the functionality among these subroutines will be apparent to the skilled person. The subroutines may be stored together in one executable file to form a self-contained program. Such an executable file may comprise computer-executable instructions, for example processor instructions and/or interpreter instructions (e.g. Java interpreter instructions). Alternatively, one or more or all of the subroutines may be stored in at least one external library file and linked with a main program either statically or dynamically, e.g. at run-time. The main program contains at least one call to at least one of the subroutines. Also, the subroutines may comprise function calls to each other. An embodiment relating to a computer program product comprises computer-executable instructions corresponding to each of the processing steps of at least one of the methods set forth. These instructions may be subdivided into subroutines and/or stored in one or more files that may be linked statically or dynamically. Another embodiment relating to a computer program product comprises computer-executable instructions corresponding to each of the means of at least one of the systems and/or products set forth. These instructions may be subdivided into subroutines and/or stored in one or more files that may be linked statically or dynamically.

The carrier of a computer program may be any entity or device capable of carrying the program. For example, the carrier may include a storage medium, such as a ROM, for example a CD ROM or a semiconductor ROM, or a magnetic recording medium, for example a floppy disc or hard disk. Further, the carrier may be a transmissible carrier such as an electrical or optical signal, which may be conveyed via electrical or optical cable or by radio or other means. When the program is embodied in such a signal, the carrier may be constituted by such a cable or other device or means. Alternatively, the carrier may be an integrated circuit in which the program is embedded, the integrated circuit being adapted for performing, or for use in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A non-invasive device for treatment of skin tissue using laser light, the device comprising:
 a light emission system configured to:
  generate:
   a first laser pulse, wherein the first laser pulse having a duration in a range between 1 and 1,000 picoseconds and a first pulse energy in a range between 0.1 and 2 mJ; and
   a subsequent second laser pulse at a predefined time delay ($\Delta T$), in a range between 1 nanosecond and 10 microseconds after the first laser pulse, wherein said second laser pulse duration being at least 10 times longer than the first pulse duration and having a second pulse energy being 10 to 100 times higher than said first pulse energy,
 an optical system configured to:
  focus the first laser pulse and the second laser pulse onto a focal spot, said focal spot positioned at a treatment location inside the skin tissue, wherein the first laser pulse having a first power density ($W/cm^2$) on the focal spot, said first laser pulse initiating a plasma in the skin tissue at the treatment location, and
  focus the second laser pulse onto the focal spot, wherein the second laser pulse having a second power density on the focal spot lower than the first power density, wherein a wavelength ($\lambda$) of the second laser pulse is selected to be included in an absorption peak of Inverse Bremsstrahlung of the plasma initiated by the first laser pulse at the treatment location to sustain or intensify the plasma initiated by the first laser pulse.

2. The non-invasive device as claimed in claim 1, wherein the first laser pulse comprises polarized light.

3. The non-invasive device as claimed in claim 1, wherein the light emission system comprises:
 a first laser configured to:
  emit the first laser pulse; and
 a second laser configured to:
  emit the second laser pulse, the second laser being different from the first laser.

4. The non-invasive device as claimed in claim 1, wherein the treatment location is in a dermis layer of said skin tissue.

5. The non-invasive device as claimed in claim 1, further comprising:
 a feedback system configured to:
  determine a focusing depth of at least one of: the first laser pulse and the second laser pulse at the treatment location.

6. The non-invasive device as claimed in claim 1, wherein the non-invasive device comprises:
 a feedback system configured to:
  detect at least one of: the plasma inside the skin tissue and an acoustic signal.

7. A method of skin treatment using laser light, the method comprising the steps of:
 generating a first laser pulse in a range between 1 and 1,000 picoseconds with a first pulse energy in a range between 0.1 and 2 mJ;
 generating a second laser pulse at a predefined time delay ($\Delta T$) after the first laser pulse, the time delay ($\Delta T$) being in a range between 1 nanosecond and 10 microseconds, said second laser pulse having a second pulse energy being 10 to 100 times higher than the first pulse energy and in a range between 1 and 200 mJ; and
 focusing the first laser pulse and the second laser pulse onto a focal spot at a treatment location inside a skin tissue, the first laser pulse having a first power density ($W/cm^2$) on the focal spot initiating a plasma in the skin tissue at the treatment location, and the second laser pulse having a second power density on the focal spot, wherein a wavelength ($\lambda$) of the second laser pulse is selected to be included in an absorption peak of Inverse Bremsstrahlung of the plasma initiated by the first laser pulse at the treatment location, wherein said second laser pulse sustains or intensifies the plasma initiated by the first laser pulse.

8. The method as claimed in claim 7, wherein the first laser pulse is generated by a first laser and the second laser pulse is generated by a second laser different from the first laser.

* * * * *